United States Patent
Sato et al.

(10) Patent No.: US 8,343,422 B2
(45) Date of Patent: Jan. 1, 2013

(54) WATER VAPOR PLASMA GENERATING APPARATUS, STERILIZATION AND DISINFECTION METHOD, AND METHOD FOR ANTIOXIDATIVE TREATMENT USING WATER VAPOR PLASMA

(75) Inventors: Chokichi Sato, Tokyo (JP); Hisaharu Ohki, Sagamihara (JP); Toshihiko Hanai, Yokohama (JP); Kenkichi Sato, Tokyo (JP); Kunio Sato, Narashino (JP); Akio Koga, Tokyo (JP); Akira Yamamoto, Hirakata (JP)

(73) Assignees: Chokichi Sato, Tokyo (JP); Hisaharu Ohki, Kanagawa (JP)

( * ) Notice: Subject to any disclaimer, the term of this patent is extended or adjusted under 35 U.S.C. 154(b) by 144 days.

(21) Appl. No.: 13/057,984

(22) PCT Filed: Jul. 6, 2009

(86) PCT No.: PCT/JP2009/062295
§ 371 (c)(1),
(2), (4) Date: Feb. 7, 2011

(87) PCT Pub. No.: WO2010/016347
PCT Pub. Date: Feb. 11, 2010

(65) Prior Publication Data
US 2011/0165299 A1    Jul. 7, 2011

(30) Foreign Application Priority Data

Aug. 8, 2008 (JP) .................................. 2008-206451
Feb. 17, 2009 (JP) .................................. 2009-034635
Apr. 20, 2009 (JP) .................................. 2009-102269

(51) Int. Cl.
*A61L 2/00* (2006.01)
(52) U.S. Cl. ... 422/28; 422/23; 315/111.21; 315/111.51
(58) Field of Classification Search .................... 422/22, 422/23, 28; 315/111.21, 111.41, 111.51
See application file for complete search history.

(56) References Cited

U.S. PATENT DOCUMENTS

| 5,603,895 A | 2/1997 | Martens et al. |
| 5,633,424 A | 5/1997 | Graves et al. |
| 5,753,196 A | 5/1998 | Martens et al. |
| 5,920,799 A | 7/1999 | Graves et al. |
| 6,159,422 A | 12/2000 | Graves et al. |

(Continued)

FOREIGN PATENT DOCUMENTS

JP    06-343820    12/1994

(Continued)

OTHER PUBLICATIONS

International Search Report dated Jul. 28, 2009, App. No. PCT/JP2009/062295.

*Primary Examiner* — Sean E Conley
(74) *Attorney, Agent, or Firm* — Knobbe, Martens, Olson & Bear LLP

(57) ABSTRACT

A water vapor plasma generating apparatus which is able to generate water vapor plasma stably is provided. By applying the water vapor plasma generated by the apparatus to an object to be treated, a sterilization and disinfection treatment can be performed. In addition, by applying the water vapor plasma generated by the apparatus to a substance containing an oily ingredient, an antioxidative treatment can be performed.

6 Claims, 5 Drawing Sheets

U.S. PATENT DOCUMENTS

| | | |
|---|---|---|
| 6,291,938 B1 * | 9/2001 | Jewett et al. ............. 315/111.51 |
| 2001/0024887 A1 | 9/2001 | Graves et al. |

FOREIGN PATENT DOCUMENTS

| JP | 07-258682 | 10/1995 |
|---|---|---|
| JP | 09-262459 | 10/1997 |
| JP | 11-012592 | 1/1999 |
| JP | 2001-308070 | 11/2001 |
| JP | 2008-013630 | 1/2008 |
| JP | 2008-188032 | 8/2008 |
| WO | WO 2004/068033 A1 | 8/2004 |
| WO | WO 2007/013160 A1 | 2/2007 |

* cited by examiner

WATER VAPOR PLASMA GENERATING APPARATUS, STERILIZATION AND DISINFECTION METHOD, AND METHOD FOR ANTIOXIDATIVE TREATMENT USING WATER VAPOR PLASMA

TECHNICAL FIELD

The present invention relates to a water vapor plasma generating apparatus, a sterilization and disinfection method and a method for an antioxidative treatment using water vapor plasma.

BACKGROUND ART

Conventionally, there is known a sterilization and disinfection apparatus for a food or the like, which uses heated water vapor, for example (see WO 2004/068003). Specifically, a object to be heated comprising a plurality of balls or the like is filled in a cylindrical body, water-jet is supplied to one side of the cylindrical body, and heated water vapor is squirted from the other side of the cylindrical body by high-frequency induction heating of the object to be heated via an exciting coil that wraps around the periphery of the cylindrical body. An apparatus by which this heated water vapor is sprayed into a food or the like to perform sterilization and disinfection is described.

In addition, in the fields of processed foods, supplements, drugs, quasi drugs, cosmetics, feeding stuff, and the like containing an oily ingredient such as edible oils, unsaturated fatty acids, phospholipids, and fat-soluble vitamins, antioxidative strategies using various antioxidative substances in manufacturing steps or packages have been investigated for controlling oxidation of the oily ingredient. As examples of these antioxidative methods, a method of adding hydroxy acid (see Japanese Patent Application Laid-Open No. Hei 07-258682), a method of adding soy sauce oil produced as a byproduct in the process of brewing soy sauce (see Japanese Patent Application Laid-Open No. Hei 11-012592), a method of adding α-lipoic acid so as to impart antioxidative property (see Japanese Patent Application Laid-Open No. 2008-013630), and the like have been investigated.

On the other hand, as for water vapor plasma, it has been investigated to use water vapor plasma for processing exhaust gas (see Japanese Patent Application Laid-Open No. Hei 6-343820), or for decomposing organic halogen (see Japanese Patent Application Laid-Open No. Hei 9-262459). However, the water vapor plasma used as above was unstable, or center temperature in the plasma was very high with 10,000 degrees centigrade. In addition, it has been investigated to use water vapor plasma for etching (see Japanese Patent Application Laid-Open No. 2001-308070), but it uses a conventional method of generating plasma between electrodes, which has a problem in supplying plasma stably. In addition, it has been investigated to generate plasma by adjusting pressure and voltage to be predetermined values so as to use the plasma for sterilizing medical appliances or the like (see Japanese Patent Application Laid-Open No. 2008-188032), but the apparatus cannot be applied to a food or the like.

SUMMARY OF THE INVENTION

Problems to be Solved by the Invention

There was a case that sufficient sterilization and disinfection effect could not be obtained with the above sterilization and disinfection apparatus using heated water vapor because of unstable temperature of the heated water vapor or other reasons. In addition, there occurred a problem that if high temperature heated water vapor was sprayed into an object to be treated such as a food for a long period in order to obtain the sterilization and disinfection effect forcedly, nutrient ingredients or the like in the food or the like were denatured or decomposed.

The present invention has been made in view of the above-mentioned facts, and an object of the present invention is to provide a water vapor plasma generating apparatus capable of stably generating water vapor plasma capable of sterilizing and disinfecting a large amount of object to be treated in a short period of time, and applying an antioxidative treatment to a substance containing an oily ingredient similarly.

Means to Solve the Problems

The present inventors repeated the studies focusing on atoms and molecules of plasma having very high activity, found that an apparatus comprising a plurality of members to be heated having a certain structure is capable of generating water vapor plasma stably, and thus, completed the present invention. In addition, it was found that by applying the water vapor plasma generated by the plasma generating apparatus to an object to be treated the sterilization and disinfection effect were obtained by treating for a short period of time. Further, it was found that oxidization of unsaturated fatty acids which were easily oxidized in the air was prevented by treating a food containing an oily ingredient with the water vapor plasma generated by the plasma generating apparatus.

That is, the present invention provides a water vapor plasma generating apparatus comprising:

a conductive object to be heated which discharges inflow water vapor as water vapor plasma; and a coil which wraps around the object to be heated and is supplied with a high-frequency wave to heat the object to be heated by electromagnetic induction, wherein the object to be heated comprises a plurality of members to be heated provided continuously and integrally from an inlet side of the water vapor toward an outlet side of the water vapor plasma, wherein through-holes which gradually decrease in number as disposed positions thereof shift from the inlet side of the water vapor toward the outlet side of the water vapor plasma, and concave portions which constitute passing regions for the water vapor together with the through-holes on at least one of surfaces opposed to each other are formed in the plurality of members to be heated, and wherein the coil comprises a hollow tube at a center of its wiring body and the hollow tube is a flow path where a coolant flows.

The present invention further provides a sterilization and disinfection method for an object to be treated comprising a step of applying the water vapor plasma generated by the apparatus to the object to be treated.

The present invention further provides a method for an antioxidative treatment for an oily ingredient comprising a step of applying the water vapor plasma generated by the apparatus to a substance containing the oily ingredient.

The present invention further provides a method for manufacturing a food comprising a step of applying the water vapor plasma generated by the apparatus to the food.

Advantages of the Invention

According to the present invention, a water vapor plasma generating apparatus which is capable of generating water vapor plasma stably can be provided. In addition, because water vapor plasma can be generated stably, the sterilization and disinfection treatment of a food can be easily performed without destroying nutrients in the food by applying such water vapor plasma to an object to be treated such as the food. As a result, the food or the like can be kept in the good state of preservation in hot and humid areas.

In addition, when the water vapor plasma is applied to a substance containing an oily ingredient, an antioxidative treatment of the substance containing an oily ingredient can be performed easily by the simple method for a very short period of time without destroying components in the substance. As a result, the storage period of foods, supplements, drugs, or the like containing an oily ingredient can be extended remarkably. Further, as for a food difficult to be put on the market because of an unsuccessful antioxidative treatment, the food can also be applied with an antioxidative treatment by the simple method to be put on the market.

MODES FOR CARRYING OUT THE INVENTION

Figure 1:
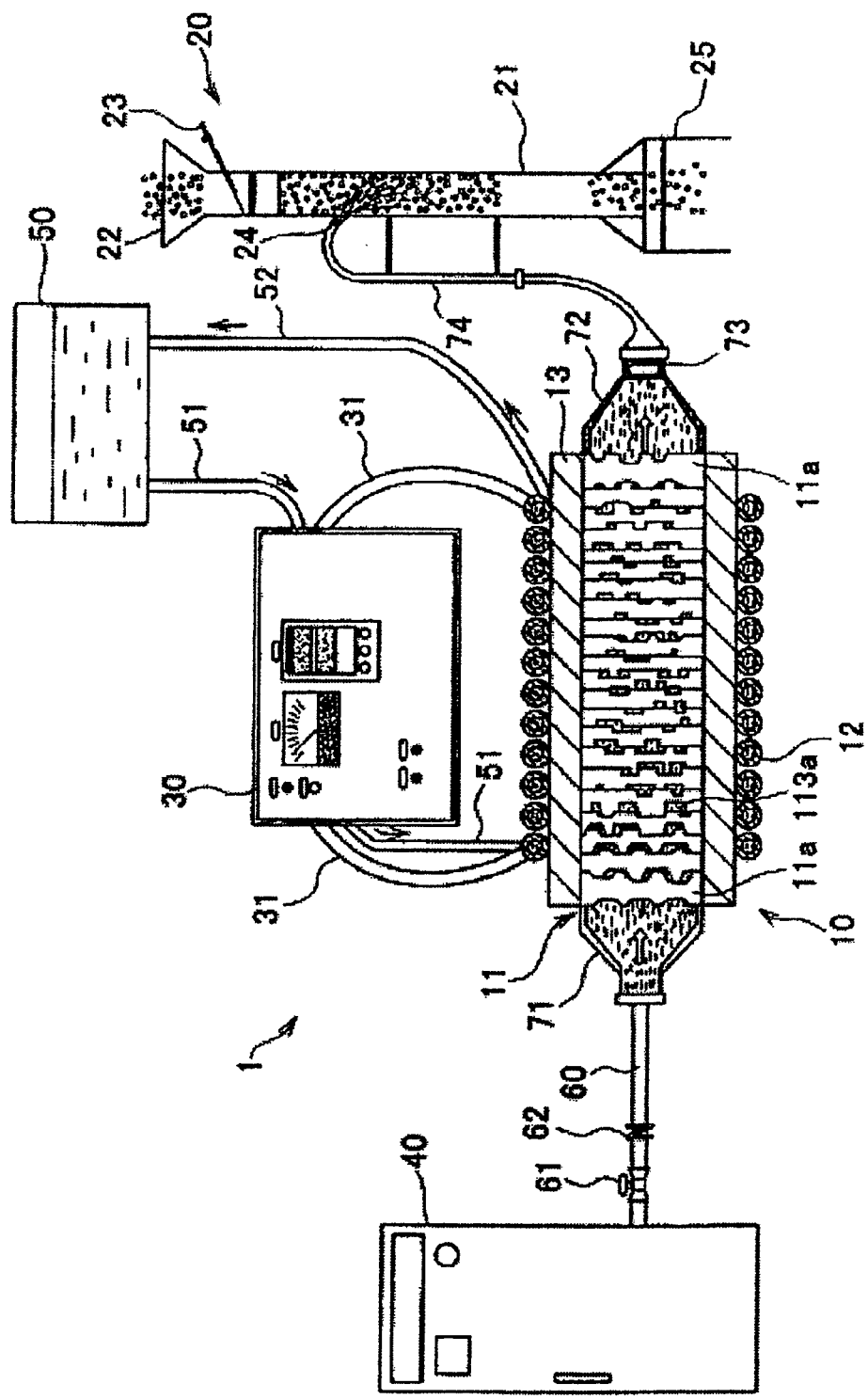
FIG. 1 illustrates an example of a water vapor plasma generating apparatus that is used for the present invention.

A water vapor plasma generating apparatus of the present invention comprises a object to be heated, and a coil for heating the object to be heated by electromagnetic induction. Water vapor flowing into the object to be heated is heated in the object to be heated and becomes an ionized state to be discharged as water vapor plasma.

The object to be heated for heating the water vapor is wrapped around by the coil for electromagnetic induction heating. When the coil is supplied with a high-frequency wave, the object to be heated is heated by electromagnetic induction. The member to be heated is required to be a conductive member so as to be heated by electromagnetic induction. In addition, as described later, it is preferred that the water vapor plasma of the present invention have a temperature of 250 to 850 degrees centigrade. Therefore, the member to be heated is preferably made of a material having stability even at a temperature of 850 degrees centigrade. Concrete examples include iron, stainless steel, copper, or the like. The water vapor which flows in is heated by the object to be heated, preferably up to a temperature of 250 degrees centigrade or higher. It is because water vapor plasma is stably generated when the temperature is 250 degrees centigrade or higher. In this case, it is preferred that an output power of the high-frequency wave be 30 kW or higher. It is for a purpose of generating water vapor plasma stably.

The member to be heated comprises a plurality of members to be heated provided continuously and integrally from an inlet side of the water vapor toward an outlet side of the water vapor plasma. In addition, through-holes which decrease in number as disposed positions thereof shift from the inlet side of the water vapor toward the outlet side of the water vapor plasma, and concave portions which constitute passing regions for the water vapor together with the through-holes in at least one of surfaces opposed to each other are formed in the plurality of members to be heated.

With such a structure, the water vapor flowing in the object to be heated becomes high temperature by the object to be heated that was heated by electromagnetic induction, and passes through the through-holes which decrease in number toward the outlet side and concave portions which constitute passing regions for the water vapor. In this case, the passing regions in the members to be heated are restricted gradually toward the outlet side. Therefore, the water vapor expands gradually while colliding against the disk members to be heated, and the force to pass through the through-holes is gradually increased. As a result, the water vapor becomes an ionized state and is discharged as water vapor plasma.

In addition, in order to stabilize the temperature of the fluid passing through the object to be heated and to prevent heating of the coil itself, the coil wrapping around the object to be heated has a hollow tube in the center of its wiring body, and it is necessary to flow coolant in the hollow tube. The coolant is not specifically limited, but it is preferred to use water because of cost. In addition, the coolant temperature is not specifically limited, but it may be approximately 10 to 40 degrees centigrade close to room temperature if cooling water is used.

A plasma generating apparatus according to an embodiment of the present invention is described below with reference to the drawings.

A plasma treatment apparatus 1 is an apparatus for sterilizing and disinfecting microorganisms such as general live bacteria, coliform bacteria and spore forming bacteria, and vermin existing on the surface of an object to be treated such as foods, foodstuffs, materials, and drugs by using water vapor plasma generated by a water vapor plasma generating apparatus 10. In addition, the plasma treatment apparatus 1 is an apparatus for applying an antioxidative treatment to a substance containing an oily ingredient such as foods, supplements, drugs, quasi drugs, cosmetics, and feeding stuffs by using water vapor plasma generated by the water vapor plasma generating apparatus 10.

As illustrated in FIG. 1, the plasma treatment apparatus 1 comprises the water vapor plasma generating apparatus 10, a treatment chamber 20, an inverter 30, a water vapor boiler 40, and a coolant tank 50.

The water vapor plasma generating apparatus 10 is an apparatus for generating water vapor plasma that is applied to an object to be treated such as a food. The water vapor plasma generating apparatus 10 comprises a object to be heated 11, a coil 12 for heating the object to be heated 11 by electromagnetic induction, a heat insulator 13 for covering the object to be heated 11 for thermal insulation, a water vapor inlet portion 71 for the water vapor generated by the water vapor boiler 40 to flow into the object to be heated 11, a water vapor plasma discharging portion 72 in order to discharge the water vapor plasma generated from the object to be heated 11, and a jet nozzle 73 to eject the water vapor plasma into the treatment chamber 20. Note that the water vapor plasma generating apparatus 10 is protected by an insulating cover made of a plastic material (not shown).

The object to be heated 11 is heated by electromagnetic induction with the coil 12 which is supplied with a high-frequency current from the inverter 30. The object to be heated 11 preferably consists of a plurality of disk members to be heated 11a having conductivity. The object to be heated is not necessarily a disk member, but is preferred to be a disk member in view of efficiency in electromagnetic induction heating of the object to be heated with the coil. The disk object to be heated 11a is made of a conductive material, for example, a metal such as iron, stainless steel, nickel, or titanium, or a conductive ceramic material such as carbon ceramic.

Figure 2:
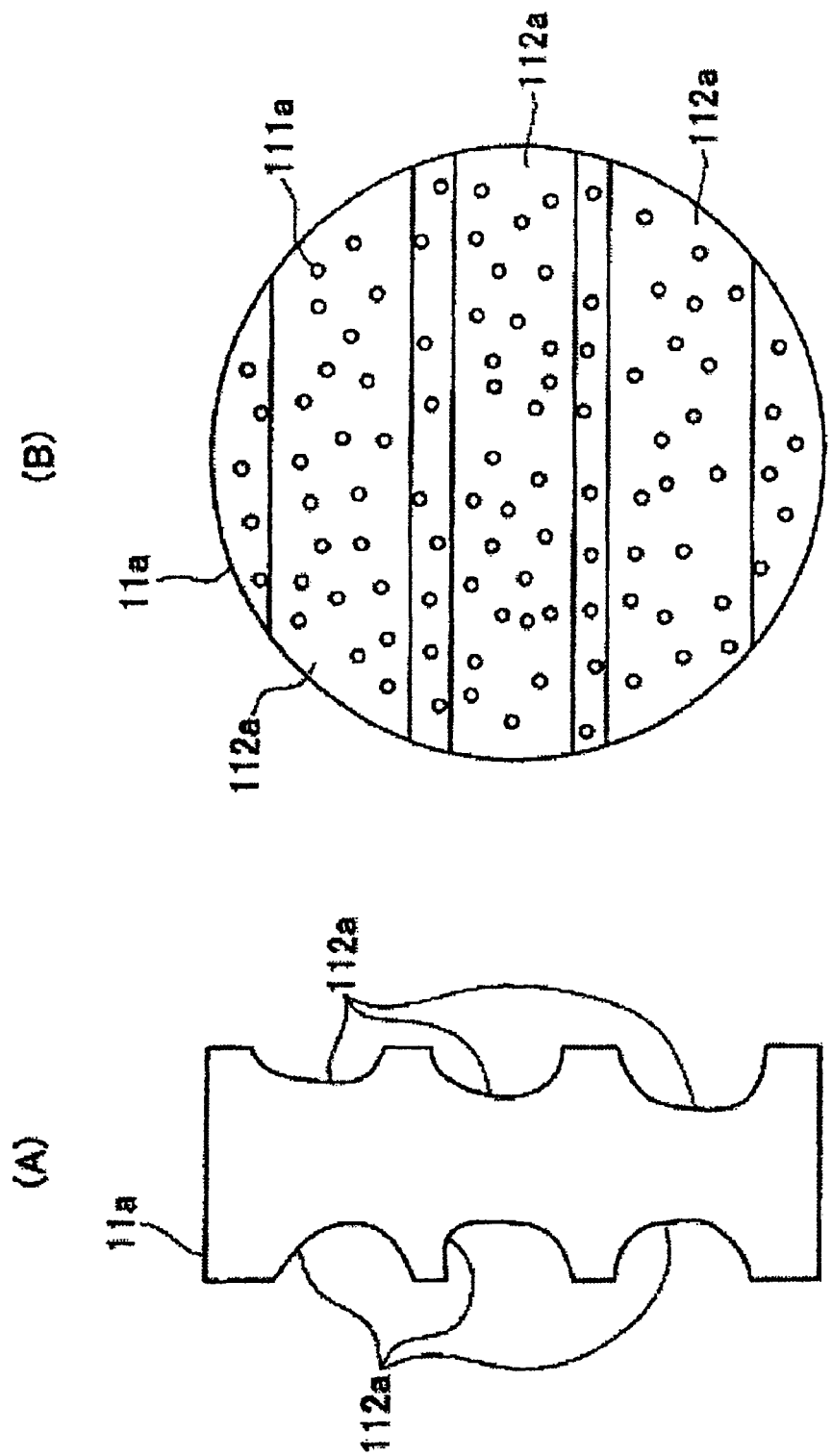
FIG. 2(A) is a side view of an example of a disk object to be heated which is disposed at an extremity of a side into which water vapor flows from a water vapor boiler.
FIG. 2(B) is a front view of the disk object to be heated illustrated in FIG. 2(A)
Figure 3:
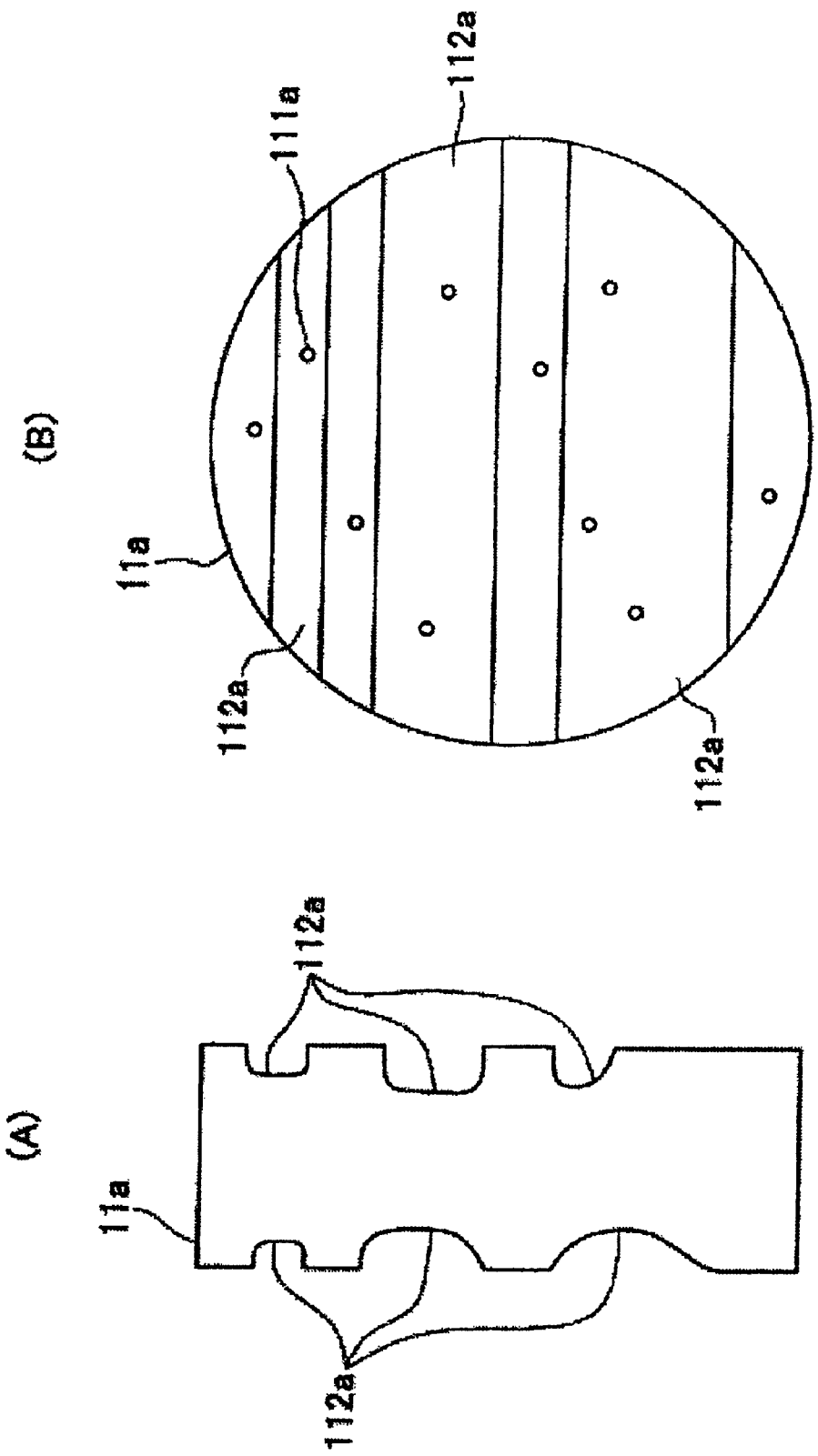
FIG. 3(A) is a side view of an example of a disk object to be heated which is disposed at an extremity of a side from which water vapor plasma is discharged.
FIG. 3(B) is a front view of the disk object to be heated illustrated in FIG. 3(A)

The plurality of disk members to be heated 11a are provided continuously and integrally from an inlet side of the water vapor from the water vapor boiler 40 toward the outlet side of the water vapor plasma, as illustrated in FIG. 1. In addition, a plurality of through-holes 111a is formed in the disk object to be heated 11a as illustrated in FIGS. 2 and 3, and a plurality of grooves 112a is formed on each of the front surface and the back surface of the disk object to be heated 11a. FIG. 2 illustrates the disk object to be heated 11a that is disposed at an extremity of the side into which the water vapor flows from the water vapor boiler 40, and FIG. 3 illustrates the disk object to be heated 11a that is disposed at an extremity of the side from which the water vapor plasma is discharged.

The through-holes 111a are formed in the disk object to be heated 11a so as gradually to decrease in the number as disposed positions thereof shift from the inlet side of the water vapor from the water vapor boiler 40 toward the outlet side of the water vapor plasma. For instance, the number of the through-holes 111a formed in the disk object to be heated 11a disposed at an extremity of the side into which the water vapor flows from the water vapor boiler 40 can be 100, and the number of the through-holes 111a formed in the disk object to be heated 11a disposed at an extremity of the side from which the water vapor plasma is discharged can be 10. Note that the number of the members to be heated which are provided continuously and integrally is not specifically limited, but it is determined in accordance with an output power and a frequency of the high-frequency wave, a type and a quantity of the object to be treated, and the like.

The grooves 112a on the disk object to be heated 11a are formed irregularly, and hence spaces 113a (see FIG. 1) are formed between the plurality of disk members to be heated 11a. The water vapor flowing into the object to be heated 11 is restricted to be able to pass only through areas of the spaces 113a and the through-holes 111a, in addition the number of the through-holes 111a gradually decreases in the number while going toward the side from which the water vapor is discharged as the water vapor plasma, and therefore the passable area is restricted gradually.

The water vapor flowing into the object to be heated 11 becomes a temperature of 250 degrees centigrade or higher by the object to be heated 11 that was heated by electromagnetic induction, and passes only through the through-holes 111a which gradually decreases in number toward the outlet side and the spaces 113a, so that the passing region is gradually restricted toward the outlet side. Therefore, the water vapor expands gradually while colliding against the disk members to be heated 11a, and the force to pass through the through-holes is gradually increased. As a result, the water vapor becomes an ionized state and is discharged as water vapor plasma. Note that despite the passing region being restricted gradually toward the outlet side, the water vapor flowing in does not flow backward. In addition, the water vapor flowing into the object to be heated 11 is heated by electromagnetic induction, but the water vapor plasma is apt not to be generated stably if the heated water vapor is lower than 250 degrees centigrade.

In the discharged water vapor plasma, positively and negatively charged particles move around at high speed, and a large Coulomb force is exerted between the charged particles, so that the kinetic energy of the particles becomes much larger than that of electrically neutral gas such as a superheated vapor. For example, because highly active neutral atoms and molecules such as hydrogen atoms, oxygen atoms, or OH radicals in the water vapor, whose bonds were cut off by the high energy particles, exist in the plasma, the water vapor plasma has a high disinfecting and sterilizing ability, and further an antioxidative function.

In order to manufacture the object to be heated 11, firstly the through-holes 111a and the grooves 112a are formed in a plurality of rectangular plates. After that, the individual rectangular plates are joined by welding. Then, the joined plurality of rectangular plates may be used as the object to be heated on its own, or they may be further formed into a disk shape by lathe to obtain the object to be heated.

The coil 12 has a hollow tube in the center of its wiring body, and coolant is supplied to the hollow tube via an inlet hose 51 so that heating of the coil 12 itself can be prevented and that the fluid passing through the object to be heated 11 can have a stable temperature. If the coolant is not supplied to the coil 12, temperature of the fluid passing through the object to be heated 11 becomes unstable, so that water vapor plasma cannot be generated.

The inverter 30 is an apparatus for applying high-frequency induction heating to the object to be heated 11 via the coil 12. A high-frequency inverter is used as the inverter 30, and it is preferred that an output power of the high-frequency wave be approximately 30 to 500 kW and a frequency thereof be 10 to 20 kHz. Note that the inverter 30 is connected electrically to the coil 12 via a conductive wire 31.

The output power of the high-frequency wave is 30 kW or higher so that the water vapor plasma can be generated stably by the water vapor plasma generating apparatus 10. Note that the inlet hose 51 of the coolant from the coolant tank 50 also passes through the inside of the inverter 30, so that a semiconductor device and the like disposed inside the inverter 30 are cooled.

The water vapor boiler 40 is connected to the water vapor plasma generating apparatus 10 by a conduit 60 via a water vapor inlet portion 71. Note that the conduit 60 is provided with an on-off valve 61 and a check valve 62 for the water vapor generated by the water vapor boiler 40.

The coolant tank 50 comprises an inlet hose 51 for the coolant to flow into one end of the wiring body of the coil 12 and for cooling the inside of the inverter 30, and an outlet hose 52 for the coolant to flow out from the other end of the wiring body of the coil 12.

The treatment chamber 20 comprises a cylindrical main body 21, an input port 22 for the object to be treated which is disposed above the main body, an input adjusting portion 23 for the object to be treated, an opening for water vapor plasma application 24 formed in the side wall of the main body 21, and an installation table 25 for supporting the main body 21. The opening for water vapor plasma application 24 is connected to a water vapor plasma leading tube 74.

Temperature of the water vapor plasma inside the main body 21 becomes stable at a temperature within a range from 250 to 850 degrees centigrade. The temperature of the water vapor plasma can be set appropriately in accordance with a type of the object to be treated.

The object to be treated is supplied from the input port 22 during the water vapor plasma which is ejected from the jet nozzle 73 of the water vapor plasma generating apparatus 10 is being ejected from the opening for water vapor plasma application 24 via the water vapor plasma leading tube 74, so that the water vapor plasma is applied to the object to be treated. Thus, the plasma application treatment is performed.

Design of the treatment chamber 20 can be modified appropriately in accordance with a type of the object to be treated. FIG. 1 illustrates the structure wherein the object to be treated is supplied from above the treatment chamber, and the water vapor plasma is instantly applied to the object to be treated while it falls by gravity, but it is also possible to adopt another structure wherein the treatment chamber is designed to be elongated in the horizontal direction, and a conveyer belt or the like is used so that the plasma can be applied for relatively long period of time. In addition, the design may be modified appropriately, for example, so that in the case of animal oil or the like, a net or the like for retaining a piece of meat may be disposed at a portion of the plasma input port in the treatment chamber and a receptacle for receiving melted oil is disposed at the lower portion.

In this way, as for the water vapor plasma generating apparatus of this embodiment the object to be heated 11 has a structure wherein the passing region for the water vapor that flows in is restricted gradually toward the outlet side. In addition, the temperature of the water vapor passing through the object to be heated 11 is stabilized by supplying the coolant to the wiring body of the coil 12, so that the high-frequency wave is able to be supplied by the inverter 30 having high output power. As a result, the water vapor plasma can be generated stably. Therefore, the water vapor plasma can be used for various purposes.

The present invention is described above with reference to the embodiment, but the present invention is not limited to the above embodiment and can be modified variously. For instance, this embodiment describes the example in which the object to be heated 11 consists of the disk members to be heated 11a, but it is sufficient that the object to be heated 11 has a structure in which the passing region for the fluid is narrowed gradually from the inlet side toward the outlet side. For instance, the member to be heated may have a block shape, a spherical shape, or an amorphous lump shape.

In addition, this embodiment describes the example in which the number of the through-holes 111a formed in the disk member to be heated 11a is decreased gradually from 100 to 10 toward the outlet side, but the number, the size, and the manner for decrease of the through-hole 111a can be determined in accordance with the number, the size, or the like of the disk members to be heated 11a themselves, the output power or the frequency of the high-frequency wave, or the type, the quantity, or the like of the object to be treated.

In addition, this embodiment describes the example in which the grooves 112a are formed on the disk member to be heated 11a to constitute the spaces 113a, but it is sufficient that a concave portion is capable of constituting the spaces 113a. For instance, the disk object to be heated may be formed so as to form a dent.

In addition, this embodiment describes the example in which the grooves 112a are formed on both sides of the disk member to be heated 11a, but the grooves 112a may be formed only on one of the surfaces of the disk members to be heated 11a opposed to each other. In addition, depending on the position where the disk member to be heated 11a is disposed, the groove 112a may not be formed.

In addition, this embodiment describes the example in which the water vapor boiler 40 is used for generating the water vapor that flows into the object to be heated 11, but it is sufficient that the apparatus is capable of generating the water vapor. For instance, water may be stored in a tank, flow out from the tank, and be electrically heated so as to generate the water vapor.

The water vapor plasma generated by the above-mentioned water vapor plasma generating apparatus is applied to a food or the like, so that sterilization and disinfection of the food or the like can be performed. In addition, if the water vapor plasma is applied to a substance containing an oily ingredient, antioxidative treatment can be performed. The structure of the treatment chamber 20 can be modified appropriately as described above in accordance with a type of the object to be treated. For instance, if the drop type chamber such as the above-mentioned treatment chamber 20 is used, the time period for which the object to be treated is applied with the water vapor plasma becomes shorter. Therefore, it is suitable especially for the sterilization and disinfection treatment of a food with small grains such as wheat, or the antioxidative treatment of a vegetable oil material such as linseed or rapeseed.

On the other hand, in the case of performing a sterilization and disinfection treatment of a food to which a high tolerant bacterium such as a spore forming bacteria group detected in soybeans adheres, or a roasting process of coffee beans, nuts, or seeds, it is preferred to use a treatment chamber having the following structure, for example.

It is preferred to use a treatment chamber comprising a treatment chamber main body, a net portion having a laterally cylindrical shape which houses an object to be treated and in turn is housed in the treatment chamber, a rotating object which comprises a screw impeller fixed to the net portion for stirring the object to be treated and is housed in the treatment chamber, a motor for rotating the rotating object, and a water vapor plasma supplying portion for supplying water vapor plasma into the treatment chamber.

Figure 4:
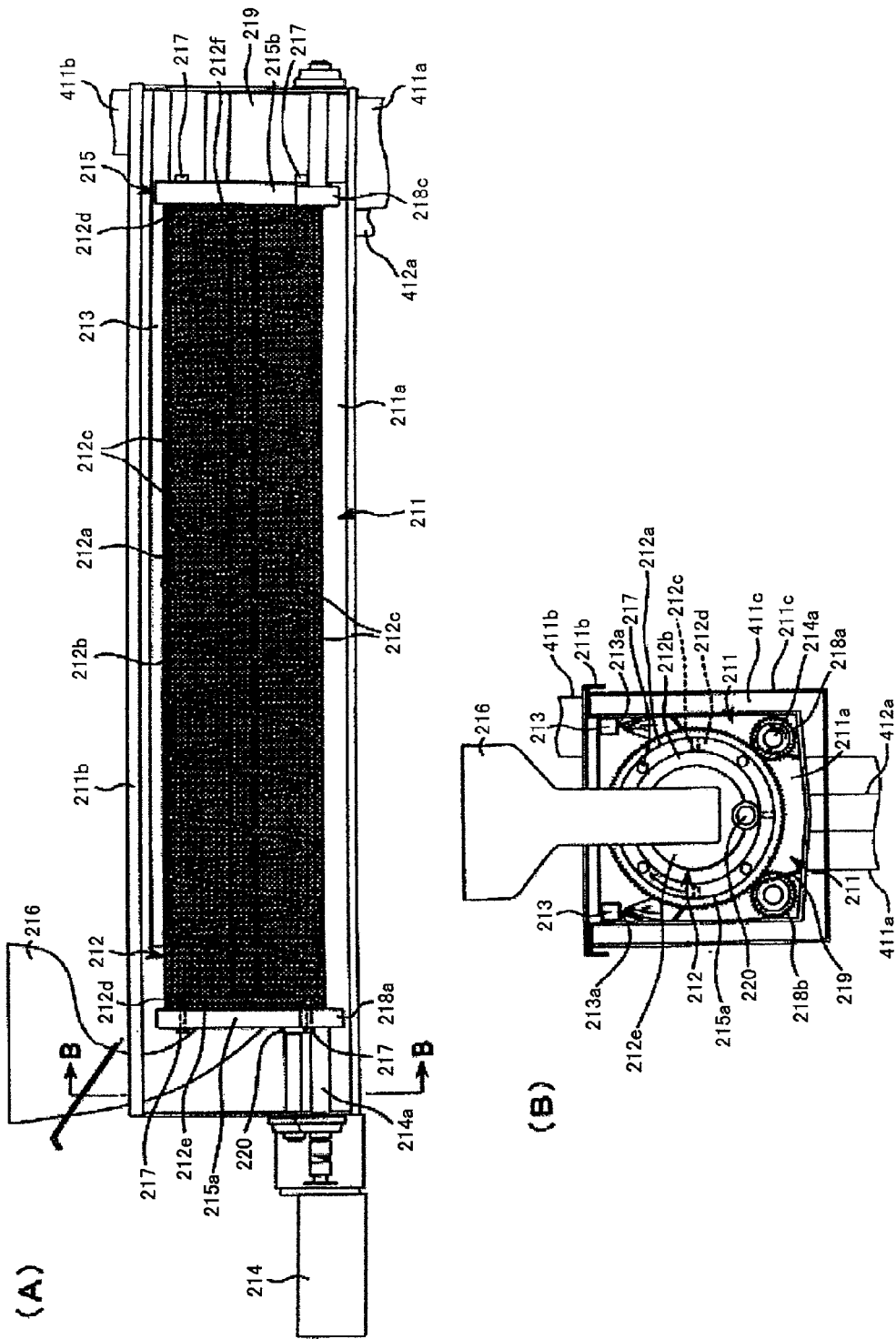
FIG. 4(A) is a sectional view illustrating one structure of a treatment chamber in which the water vapor plasma of the present invention is applied.
FIG. 4(B) is a fragmentary view taken in the direction of the arrows substantially along the arcuate line B-B of FIG. 4(A)

With reference to FIG. 4 for description, a treatment chamber 211 comprises a net-like rotating object 212 housing an object to be treated such as a food, which is housed in the treatment chamber, a water vapor plasma supplying portion 213 for supplying water vapor plasma into the treatment chamber, a motor 214 for rotating the net-like rotating object 212, a gear portion 215 (215a and 215b) for fixing the gear portion 215 and transmitting a driving force of the motor 214 to the net-like rotating object 212, an input portion 216 for supplying the object to be treated to the net-like rotating object 212, and a guiding plate 219 for taking out the object to be treated after the sterilization and disinfection, which is disposed on the opposite side to the input portion 216.

The rotating object 212 is for stirring the object to be treated that was housed during the sterilization and disinfection treatment and the antioxidative treatment. The rotating object 212 consists of a net portion 212a, a screw impeller 212b, stirring flat plates 212c, and fixing portions 212d. The net portion 212a consists of a laterally cylindrical net. A mesh size of the net portion 212a is modified in accordance with a size of the object to be treated that is housed. One end of the net portion 212a comprises an input opening 212e from which the object to be treated is supplied, and the other end of the net portion 212a comprises an output opening 212f from which the object to be treated is taken out.

The screw impeller 212b stirs the object to be treated that is housed in the net portion 212a. The screw impeller 212b is formed continuously in a helical shape and is capable of rotating about the center axis of the net portion 212a as a rotation axis. Further, the thickness of the screw impeller 212b is changed in accordance with a type of the object to be treated. Therefore, the thickness of the rotating object 212 is changed in accordance with a type of the object to be treated. Thus, as to the rotating object 212, the mesh size of the net portion 212a and the thickness of the screw impeller 212b can be adjusted in accordance with a type of the object to be treated.

The stirring flat plates 212c are housed in the net portion 212a together with the screw impeller 212b so as to stir the object to be treated. Note that the stirring flat plates 212c are used, for example, if the object to be treated is a noodle or the like, so that the rotation speed of the rotating object 12 is slow. The stirring flat plates 212c are fixed to an inner peripheral surface of the net portion 212a at a constant pitch along the extending direction of the net portion 212a.

A pair of the fixing portions 212d is for housing and fixing the rotating object 212 in the treatment chamber 212 via the gear portion 215 detachably. The fixing portion 212d is formed in a ring-like shape. The pair of fixing portions 212d is fixed to both ends of the net portion 212a, and screw holes (not shown) for engaging bolts 217 are formed in the same. Each of the fixing portions 212d is fixed the pair of gear portions 212 disposed in the treatment chamber 211 by engaging the bolts 217 with the screw holes.

The water vapor plasma supplying portion 213 is connected to the water vapor plasma generating apparatus and comprises a bifurcated tube. The water vapor plasma supplying portion 213 is disposed above the rotating object 212 in the treatment chamber 211. A plurality of holes 213a (see FIG. 4(b)) for discharging the water vapor plasma are formed in the water vapor plasma supplying portion 213.

A gear wheel 218a is fixed to a rotation shaft 214a of the motor 214 in the treatment chamber 211. The gear wheel 218a engages with a gear portion 215a on the input portion 216 side. Therefore, the driving force of the motor 214 is transmitted to the rotating object 212 via the gear wheel 218a and the gear portion 215a. A gear wheel 218b is disposed at a position in parallel to the gear wheel 218a at the lower portion in the treatment chamber 211. The gear wheel 218b also engages with the gear portion 215a on the input portion 216 side, so as to assist and support the rotation of the gear portion 215a. In addition, a bearing 220 is disposed in the treatment chamber 211 so as to guide the inner surface of the gear portion 215a for preventing the rotating object 212 from floating.

In addition, the gear portion 215b on the guiding plate 219 side also engages with gear wheels 218c and 218d provided in parallel inside the treatment chamber 211. By the gear wheels 218c and 218d, the gear portion 215b is supported and rotates smoothly.

Figure 5:
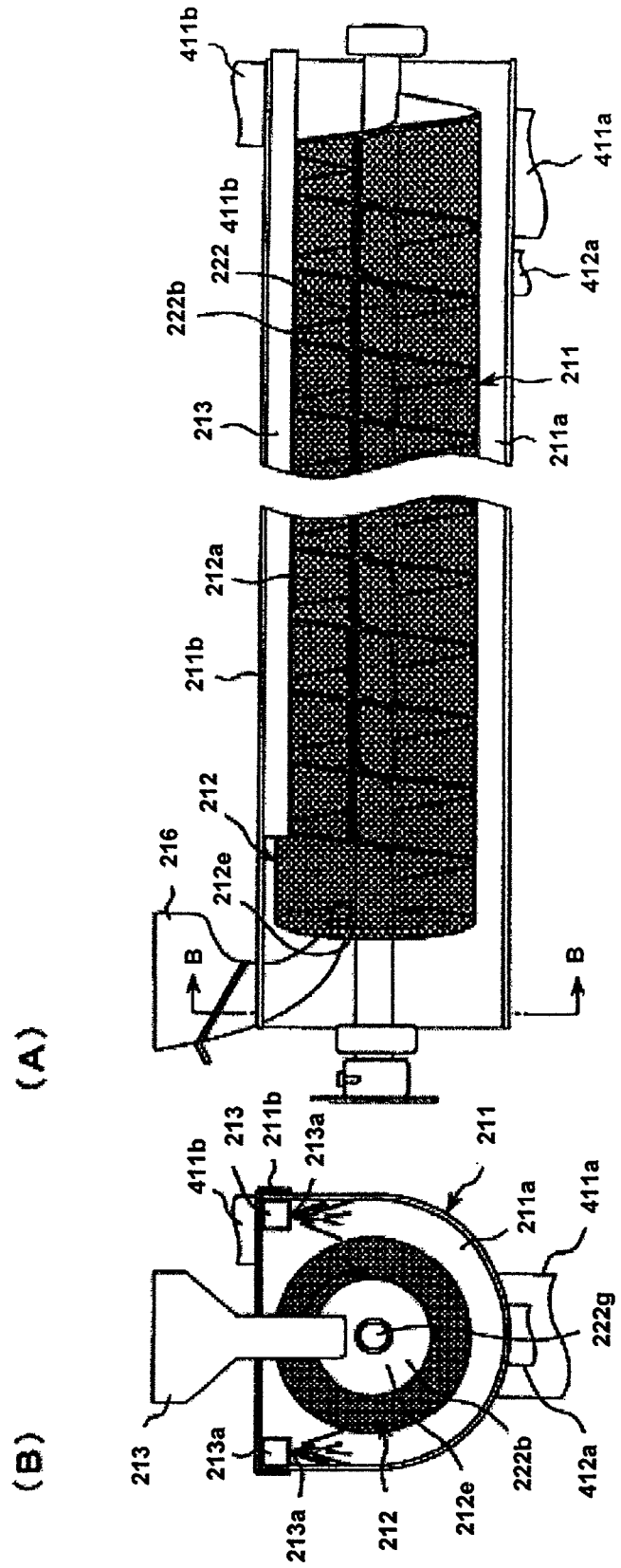
FIG. 5(A) is a sectional view illustrating one structure of a treatment chamber in which the water vapor plasma of the present invention is applied.
FIG. 5(B) is a fragmentary view taken in the direction of the arrows substantially along the arcuate line B-B of FIG. 5(A).

In addition, the treatment chamber may have a structure as illustrated in FIG. 5. Hereinafter, with reference to FIG. 5, only the part different from that illustrated in FIG. 4 is described.

In the treatment chamber 211, the rotating object 212 comprises a rotation shaft 222g. The rotation shaft 222g is formed integrally with a screw impeller 222b that is formed continuously in a helical shape. The rotation shaft 222g is detachably connected to the rotation shaft of the motor (not shown) and is supposed outside the treatment chamber 211 so as to be rotatable. Note that the rotating object 212 does not comprises the stirring flat plate 212c of the embodiment illustrated in FIG. 4.

In this embodiment, the rotation shaft 222g of the rotating object 212 is driven by the motor to rotate, so that the rotating object 212 is rotated. The rotating object 212 can be rotated with the structure that is easier than that of the first embodiment, and the same treatment as the embodiment in FIG. 4 can be performed.

The object to be treated is supplied into the treatment chamber described above, and the water vapor plasma generated by the water vapor plasma generating apparatus is applied to the object to be treated so that the sterilization and disinfection treatment can be performed. In addition, the water vapor plasma is applied to the substance containing an oily ingredient, so that the antioxidative treatment of the oily ingredient can be performed. Further, it can be used for treatment of a food such as roasting.

When the water vapor plasma according to the present invention is applied to the object to be treated for sterilization and disinfection, the sterilization and disinfection treatment can be performed in a very short period of time. Therefore, if the object to be treated is a food such as wheat, the sterilization and disinfection treatment can be performed without denaturing or damaging to nutrients such as proteins, vitamins, or minerals. The object to be treated is not particularly limited in the present invention, but in particular, in the case of a food, the present invention can be applied to various foods such as soybeans, wheat, red beans, coffee beans, noodles, and the like. In addition, the present invention can also be applied to a feeding stuff for livestock or crops, for example, a food waste, in the same manner.

Microorganisms such as general live bacteria, coliform bacteria, *Escherichia coli* and spore forming bacteria existing on the surface of the object to be treated can be sterilized and disinfected by applying the water vapor plasma, and hence it is very useful in particular for preserving a food under a hot and humid condition in which germs can easily proliferate. In addition, in the sterilization and disinfection method using the water vapor plasma according to the present invention, an effect of sterilization and disinfection can be obtained by application of the water vapor plasma to the object to be treated for 30 seconds or shorter. Depending on a type of the object to be treated, the effect can occur even for shorter time of application, and hence the application time can be set appropriately in accordance with a type of the object to be treated.

In addition, the substance containing an oily ingredient in the present invention corresponds to a substance containing an oily ingredient such as foods, supplements, drugs, quasi drugs, cosmetics, feeding stuffs, and the like containing an oily ingredient such as edible oils, unsaturated fatty acids, carotenoids, phospholipids, and fat-soluble vitamins. In addition, the concept of the substance containing an oily ingredient includes a substance in a state of containing an oily ingredient such as a composition containing an oily ingredient in a manufacturing process of a product. In addition, the composition itself containing the oily ingredient is included, and the substance in a state of containing an oily ingredient in a manufacturing process of a product is also included.

Examples of the edible oils include vegetable oils (wheat germ oil, perilla seed oil, evening primrose oil, avocado oil, almond oil, linseed oil, perilla oil, apricot kernel oil, walnut oil, purified olive oil, sesame oil, purified camelia oil, tea seed oil, oat oil, jojoba oil, borage seed oil, Yuzu seed oil, camellia oleifera seed oil, rose hip oil, horse oil, lamprey oil, soft-shelled turtle oil, cacao oil, rice bran oil, brown rice germ oil, soybean oil, cotton seed oil, rapeseed oil, palm oil, palm kernel oil, coconut oil, corn oil, earthnut oil, safflower oil, castor oil, tung oil, and the like); animal oils (for example, beef tallow, lard, chicken fat, milk fat, and egg yolk oil); fish oil (for example, sardine oil, mackerel oil, liver oil, and whale oil); and processed oils thereof (for example, fractionated oils, hydrogenated oils, and transesterified oils).

An example of the unsaturated fatty acid includes a fatty acid having one or more unsaturated bonds in a molecule. The number of carbon atoms is not particularly limited, and the example includes linolenic acid, linoleic acid, docosahexaenoic acid (hereinafter abbreviated as DHA), eicosapentaenoic acid (hereinafter abbreviated as EPA), arachidonic acid, and derivatives, isomers and the like thereof.

Examples of the carotenoid include components of α-, β-, and ν-carotene, capsaxanthin, astaxanthin, lutein, zeaxanthin, lycopene, crocin, and annatto; and extracts of algae, microorganisms, plants, animals, or the like which contain these components.

Examples of the phospholipid include soybean lecithin, egg yolk lecithin, phosphatidylcholine, sphingosine, phosphatidylethanolamine, phosphatidylinositol, phosphatidylglycerol, enzyme-treated lecithin, and fractionated lecithin.

Examples of the fat-soluble vitamin include vitamin A; for example, fatty acid esters such as vitamin A acetate and vitamin A palmitate, and vitamin A oils.

The sterilization and disinfection treatment and the antioxidative treatment according to the present invention may be performed, in a case of a food, by applying the water vapor plasma to a raw material or applying the water vapor plasma to a processed material. For instance, in the case of the antioxidative treatment of the vegetable oil as a food, it is possible to apply the water vapor plasma to rapeseed or linseed as a raw material thereof in the raw state and afterward to perform oil pressing, or it is possible to perform oil pressing first, and afterward to apply the water vapor plasma. In addition, it is possible to use a raw material which has been roasted. In the case of the animal oil, it is possible to apply the water vapor plasma to a piece of meat such as beef or pork directly so that the oil is melted and obtained, or to apply the water vapor plasma to oil obtained by a wet rendering method or the like.

In the case of supplements, drugs, quasi drugs, or cosmetics, it is possible to apply the water vapor plasma only to the composition containing an oily ingredient first, and afterward to obtain the target product, or to apply the water vapor plasma to the obtained target product.

As described above, if a food or the like is applied with the water vapor plasma generated from the water vapor plasma generating apparatus according to the present invention, various effects such as disinfection and antioxidation can be obtained. For instance, the effect of the present invention also covers a food manufactured by the step of applying the water vapor plasma of the present invention to coffee beans, nuts, or tea leaves on a purpose of roasting.

In the present invention, the effect of antioxidation can be determined by measuring AV (acid value) or POV (peroxide value), for example. Specifically, in the case of a food, if the AV is 2 or higher, or if the POV is 20 or higher, it can be determined that oxidation is proceeding. In addition, if an oily ingredient is oxidized, there is a smell of so-called "back smell" or "deterioration smell". Therefore, the effect of antioxidation can also be determined by sensing the smell.

EXAMPLES

Hereinafter, the present invention is further described in detail with reference to examples, but needless to say, the present invention is not limited to the examples.

Example 1

The treatment chamber illustrated in FIG. 5 was used as treatment chamber of the water vapor plasma generating apparatus illustrated in FIG. 1, the output power of the high-frequency wave was set to be 30 kW, the frequency thereof was set to be 20 kHz, and the temperature of the plasma was set to be 400 degrees centigrade. Then, soybeans, wheat, and red beans each were supplied into the treatment chamber and applied with the water vapor plasma. Existence of bacteria was confirmed before and after application of the water vapor plasma. The results are shown in Table 1.

TABLE 1

| Subject | Condition (temperature of water vapor plasma, temperature in treatment chamber, application period) | Coliform bacteria *1 | Number of general live bacteria *1 | Spore forming bacteria | |
|---|---|---|---|---|---|
| | | | | 48 hours | *Bacillus cereus* *2 |
| Soybean | Not treated | Negative | $2.0 \times 10^2$/g | $2.0 \times 10^1$/g | Negative |
| Soybean | 400° C., 195° C., 8 S | Negative | $4.0 \times 10^1$/g | Not detected | Negative |
| Soybean | 400° C., 195° C., 11 S | Negative | $8.0 \times 10^1$/g | Not detected | Negative |
| Soybean | 400° C., 195° C., 15 S | Negative | $3.0 \times 10^1$/g | Not detected | Negative |
| Soybean | 400° C., 195° C., 20 S | Negative | $7.0 \times 10^1$/g | Not detected | Negative |
| Wheat | Not treated | Positive | $9.4 \times 10^5$/g | $1.1 \times 10^3$/g | Positive |
| Wheat | 400° C., 195° C., 8 S | Negative | $4.0 \times 10^1$/g | Not detected | Negative |
| Wheat | 400° C., 195° C., 12 S | Negative | Not detected | Not detected | Negative |
| Red bean | Not treated | Negative | $1.4 \times 10^2$/g | $3.0 \times 10^1$/g | Negative |
| Red bean | 400° C., 195° C., 8 S | Negative | $1.2 \times 10^2$/g | $1.0 \times 10^1$/g | Negative |
| Red bean | 400° C., 195° C., 10 S | Negative | Not detected | Not detected | Negative |
| Red bean | 400° C., 195° C., 12 S | Negative | Not detected | Not detected | Negative |

*1 petrifilm
*2 MYP agar

As shown in Table 1, in the case of soybeans as the object to be treated, the number of general live bacteria decreased, and spore forming bacteria were not detected.

In the case of wheat as the object to be treated, it became negative for coliform bacteria, general live bacteria decreased in number or became not to be detected, spore forming bacteria became not to be detected, and it became negative for *Bacillus cereus*.

In the case of red beans as the object to be treated, general live bacteria decreased in number or became not to be detected, and spore forming bacteria decreased in number or became not to be detected.

Example 2

The drop type treatment chamber of the water vapor plasma generating apparatus illustrated in FIG. 1 was used as it was, the output power of the high-frequency wave was set to be 30 kW, and the frequency thereof was set to be 20 kHz. Then, wheat was supplied to the treatment chamber and applied with the water vapor plasma. Existence of bacteria was confirmed before and after application of the water vapor plasma. As a comparison example, a conventional sterilization and disinfection treatment using heated water vapor was performed. The results are shown in Table 2.

TABLE 2

| temperature and number of application of water vapor plasma | Number of general live bacteria | Coliform bacteria | temperature and number of application of water vapor plasma | Number of general live bacteria | Coliform bacteria |
|---|---|---|---|---|---|
| 550° C., once | $5 \times 10^3$ | 90 | — | — | — |
| 500° C., once | $2 \times 10^4$ | 0 | 500° C., once | $3 \times 10^5$ | $4 \times 10^3$ |
| 500° C., twice | <300 | 0 | — | — | — |
| 450° C., once | $1 \times 10^3$ | 0 | 450° C., once | $3 \times 10^5$ | $8 \times 10^3$ |
| 400° C., once | $1 \times 10^4$ | 10 | 400° C., once | $2 \times 10^5$ | $2 \times 10^3$ |
| — | — | — | 350° C., once | $1 \times 10^5$ | $7 \times 10^3$ |
| Not treated | $4 \times 10^5$ | $1 \times 10^4$ | Not treated | $7 \times 10^5$ | $1 \times 10^4$ |

As shown in Table 2, it can be understood that the number of general live bacteria and coliform bacteria decreased remarkably in the case of using the water vapor plasma compared with the case of using the heated water vapor.

Example 3

The drop type treatment chamber of the water vapor plasma generating apparatus illustrated in FIG. 1 was used as it was, the output power of the high-frequency wave was set to be 30 kW, the frequency thereof was set to be 20 kHz, and the temperature of the plasma was set to be 300 degrees centigrade. Then, 30 kg of raw rapeseed was supplied into the input port 22 for the object to be treated, and was kept in the position where the plasma from the opening for water vapor plasma application 24 was applied for five seconds, so that the antioxidative treatment was performed.

Next, oil pressing of the rapeseed after the antioxidative treatment was performed, and hence 20 liters of rapeseed oil was obtained. After that, the obtained rapeseed oil was filled and sealed in a transparent container made of polypropylene, and was stored in a cool and dark place at room temperature as it was for 36 months.

Test Example 1

(1) Color change about the container was visually confirmed, and there was no change in color.
(2) A lid of the container was opened, and smell of the oil was sensed, and there was no back smell or deterioration smell.
(3) AV (acid value) test or POV (peroxide value) test were performed for measuring a degree of oxidization of the oil. The AV test was performed by using AV-CHECH paper (made by TOYO filter paper CO., Ltd), and the POV test was performed by using POV test paper (made by SHIBATA SCIENTIFIC TECHNOLOGY LTD). As a result of the AV test, AV values in a range of 0.5 to 1.0 were obtained. In addition, as a result of the POV test, POV values in a range of 0 to 10 were obtained. According to the measurement by the AV value, it can be determined that there is little oxidization of the oil if the AV value is 2 or smaller. In addition, according to the measurement by the POV value, it can be determined that there is little oxidization of the oil if the POV value is 20 or smaller.

From these results, it is understood that the rapeseed oil after performing the antioxidative treatment of the present invention is not oxidized after the lapse of 36 months.

Example 4

The net made of iron is disposed in the treatment chamber of the water vapor plasma generating apparatus illustrated in FIG. 1 so that chicken meat, beef, or pork was retained at the opening for water vapor plasma application 24 and applied with the water vapor plasma at 300 degrees centigrade for melting the chicken meat, the beef, or the pork to obtain oil. The piece of meat applied with the water vapor plasma was melted instantly to be oil dropping, and the obtained oil was stored in a receiving container (not shown). The obtained chicken oil is referred to as Sample 1, the obtained beef oil is referred to as Sample 3, and the obtained pork oil is referred to as Sample 5.

Comparison Example 1

The wet rendering method that is normally used for obtaining animal oil was used so as to obtain oil from chicken meat, beef, and pork. The thus obtained chicken oil is referred to as Sample 2, the thus obtained beef oil is referred to as Sample 4, and the thus obtained pork oil is referred to as Sample 6.

Test Example 2

The oils obtained in Example 2 described above and the oils obtained in Comparison example 1 were stored in a dark place at 40 degrees centigrade, and changes in AV values and POV values thereof with the passage of time were measured.

The above-mentioned Samples 1 to 6 were stored by 20 grams each in an 100 gram vial, total six vials, which were sealed and stored in a dark place at 40 degrees centigrade. The start time point of the storage is referred to as 0 week, and AV values and POV values were measured at 1 to 4 weeks each. The results are shown in Tables 3 and 4.

TABLE 3

| Change in AV values with the passage of time | | | | | |
|---|---|---|---|---|---|
| | 0 w | 1 w | 2 w | 3 w | 4 w |
| Sample 1 (chicken oil applied with plasma) | 0.81 | 0.90 | 1.10 | 0.84 | 1.11 |
| Sample 2 (ordinarily prepared chicken oil) | 1.08 | 1.02 | 1.20 | 0.98 | 1.16 |
| Sample 3 (beef oil applied with plasma) | 1.72 | 1.80 | 1.90 | 1.88 | 1.83 |
| Sample 4 (ordinarily prepared beef oil) | 2.12 | 1.91 | 2.20 | 2.31 | 2.57 |
| Sample 5 (pork oil applied with plasma) | 0.97 | 1.16 | 0.70 | 1.17 | 1.30 |
| Sample 6 (ordinarily prepared pork oil) | 1.25 | 2.79 | 2.10 | 2.90 | 3.00 |

TABLE 4

Change in POV values with the passage of time

|  | 0 w | 1 w | 2 w | 3 w | 4 w |
|---|---|---|---|---|---|
| Sample 1 (chicken oil applied with plasma) | 1.0 | 3.3 | 6.3 | 7.0 | 8.4 |
| Sample 2 (ordinarily prepared chicken oil) | 5.2 | 9.2 | 11.9 | 15.2 | 21.2 |
| Sample 3 (beef oil applied with plasma) | 0.9 | 1.8 | 1.7 | 1.0 | 1.9 |
| Sample 4 (ordinarily prepared beef oil) | 8.5 | 8.7 | 10.1 | 9.3 | 10.3 |
| Sample 5 (pork oil applied with plasma) | 3.5 | 4.0 | 4.6 | 4.2 | 5.4 |
| Sample 6 (ordinarily prepared pork oil) | 4.5 | 9.2 | 20.5 | 38.5 | 53.5 |

It is understood that oil obtained by applying the water vapor plasma is not oxidized as much as oil obtained by the normal method.

Test Example 3

The rapeseed oil obtained in Example 3 (after 36 months of storage) was used for frying tempura. The fried tempura was put in a transparent plastic bag for food made of polypropylene and was sealed with air in the bag, which was stored. It was stored at a bright place under direct sunlight at 40 degrees centigrade.

When 23 days passed, change in color was visually checked, and there was no change in color and no mold or the like. In addition, the bag was opened and smell of the tempura was confirmed. There was neither back smell nor deterioration smell.

INDUSTRIAL APPLICABILITY

The water vapor plasma generated by the water vapor plasma generating apparatus of the present invention has the sterilization and disinfection function, as well as an antioxidative function. The sterilization and disinfection method of the present invention enables the sterilization and disinfection treatment without destroying components of a food with a simple method. In addition, the antioxidative treatment method of the present invention can be applied to various industry fields such as foods that are substances containing an oily ingredient, supplements, drugs, quasi drugs, cosmetics, and feeding stuffs. In addition, concerning a food that is difficult to preserve for long period because of existence of microorganism or a product for which a short expiration date is set because of oxidization progress, the preservation period or the expiration date can be expanded outstandingly, and hence the industrial usefulness is very large.

REFERENCE SIGNS LIST

| 1 | water vapor plasma treatment apparatus |
|---|---|
| 10 | water vapor plasma generating apparatus |
| 11 | object to be heated |
| 11a | disk member to be heated |
| 12 | coil |
| 13 | heat insulator |
| 20 | treatment chamber |
| 21 | treatment chamber main body |
| 22 | input port for the object to be treated |
| 23 | input adjusting portion for the object to be treated |
| 24 | opening for water vapor plasma application |
| 25 | installation table |
| 30 | inverter |
| 31 | conductive wire |
| 40 | water vapor boiler |
| 50 | coolant tank |
| 51 | inlet hose |
| 52 | outlet hose |
| 60 | conduit |
| 61 | on-off valve |
| 62 | check valve |
| 71 | water vapor inlet portion |
| 72 | water vapor plasma discharging portion |
| 73 | jet nozzle |
| 74 | water vapor plasma leading tube |
| 111a | through-hole |
| 112a | groove |
| 113a | space |
| 211 | treatment chamber |
| 211a | treatment chamber main body |
| 211b | top cover |
| 212 | rotating object |
| 212a | net portion |
| 212b | screw impeller |
| 212c | stirring flat plate |
| 212d | fixing portion |
| 212e | input opening part |
| 213 | water vapor supplying portion |
| 214 | motor |
| 215 | gear portion |
| 216 | input portion |
| 217 | bolt |
| 218 | gear wheel |
| 219 | guiding plate |
| 222b | screw impeller |
| 222g | rotation shaft |

The invention claimed is:

1. A water vapor plasma generating apparatus comprising:
a conductive object to be heated which discharges inflow water vapor as water vapor plasma; and
a coil which wraps around said object to be heated and is supplied with a high-frequency wave to heat said object to be heated by electromagnetic induction,
wherein said object to be heated comprises a plurality of members to be heated provided continuously and integrally from an inlet side of the water vapor toward an outlet side of the water vapor plasma,
wherein through-holes which gradually decrease in number as disposed positions thereof shift from the inlet side of the water vapor toward the outlet side of the water vapor plasma, and concave portions which constitute passing regions for the water vapor together with said through-holes on at least one of surfaces opposed to each other are formed in said plurality of members to be heated, and
wherein said coil comprises a hollow tube at a center of its wiring body and said hollow tube is a flow path where a coolant flows.

2. The water vapor plasma generating apparatus according to claim 1, wherein the temperature of said discharged water vapor plasma is 250 degrees centigrade or higher.

3. The water vapor plasma generating apparatus according to claim 1, wherein output power of said high-frequency wave is 30 kW or higher.

4. A sterilization and disinfection method for an object to be treated, comprising a step of applying the water vapor plasma generated by the water vapor plasma generating apparatus according to any one of claims 1 to 3 to the object to be treated.

5. A method for an antioxidative treatment for a substance containing an oily ingredient, comprising a step of applying the water vapor plasma generated by the water vapor plasma generating apparatus according to any one of claims 1 to 3 to the substance containing an oily ingredient.

6. A method for manufacturing a food, comprising a step of applying the water vapor plasma generated by the water vapor plasma generating apparatus according to any one of claims 1 to 3 to the food.

* * * * *